(12) United States Patent
Meurville et al.

(10) Patent No.: US 8,500,637 B2
(45) Date of Patent: Aug. 6, 2013

(54) VISCOSIMETRIC BIOSENSOR FOR MONITORING ANALYTE LEVELS

(75) Inventors: Eric Meurville, Chaffois (FR); Jean-Michel Sallese, Pully (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 418 days.

(21) Appl. No.: 13/054,021

(22) PCT Filed: Jul. 14, 2009

(86) PCT No.: PCT/IB2009/053041
§ 371 (c)(1),
(2), (4) Date: Jan. 13, 2011

(87) PCT Pub. No.: WO2010/007580
PCT Pub. Date: Jan. 21, 2010

(65) Prior Publication Data
US 2011/0124985 A1    May 26, 2011

(30) Foreign Application Priority Data
Jul. 14, 2008  (EP) .................................... 08160352

(51) Int. Cl.
*A61B 5/00*     (2006.01)
*G01N 11/00*   (2006.01)
*G01N 33/48*   (2006.01)

(52) U.S. Cl.
USPC ........... 600/309; 600/316; 600/365; 422/68.1; 73/54.01

(58) Field of Classification Search
USPC ................. 600/300, 309, 310, 316, 341, 345, 600/365; 73/54.01; 422/68.1
See application file for complete search history.

(56) References Cited

U.S. PATENT DOCUMENTS

| 4,926,682 A | 5/1990 | Holm-Kennedy et al. |
| 6,210,326 B1 | 4/2001 | Ehwald |
| 6,267,002 B1 * | 7/2001 | Ehwald et al. ............... 73/54.01 |

(Continued)

FOREIGN PATENT DOCUMENTS

| DE | 195 01 159 | 7/1996 |
| DE | 196 48 695 | 6/1997 |

(Continued)

OTHER PUBLICATIONS

Ballerstadt, Ralph, et al., "Concanavalin A for in vivo glucose sensing: A biotoxicity review." *Biosensors and Bioelectronics 22* (2006), pp. 275-284.

(Continued)

*Primary Examiner* — Eric Winakur
*Assistant Examiner* — Chu Chuan (JJ) Liu
(74) *Attorney, Agent, or Firm* — Faegre Baker Daniels LLP (57) ABSTRACT

The invention relates to a viscosimetric sensor for monitoring an analyte level in a patient or in body fluids ex vivo. In particular, the invention relates to a sensor for monitoring analytes, such as glucose levels in a patient. The sensor comprises at least two hermetically closed chambers (2a, 2b), including an activation chamber and a measuring chamber, containing a sensitive fluid (3), the chambers communicating with each other through at least one microchannel (5), and a semi-permeable barrier (4) allowing the analyte to enter or leave the chambers. Each said chamber comprises at least one flexible membrane (6, 7) configured for antagonistic variations of the volume of the chambers.

14 Claims, 8 Drawing Sheets

U.S. PATENT DOCUMENTS

| | | | |
|---|---|---|---|
| 6,432,050 B1 * | 8/2002 | Porat et al. | 600/309 |
| 6,458,325 B1 | 10/2002 | Roscher et al. | |
| 7,789,829 B2 | 9/2010 | Strassler et al. | |
| 8,323,193 B2 * | 12/2012 | Skerl et al. | 600/365 |
| 2001/0035047 A1 | 11/2001 | Ehwald et al. | |
| 2010/0241063 A1 * | 9/2010 | Straessler et al. | 600/365 |

FOREIGN PATENT DOCUMENTS

| | | |
|---|---|---|
| DE | 10 2008 016 121 | 7/2009 |
| WO | WO 2004/037079 | 5/2004 |
| WO | WO 2008/102001 | 8/2008 |

OTHER PUBLICATIONS

Beyer, Uwe and Ehwald, Rudolf, "Compensation of Termperature and Concanavalin A Concentration Effects for Glucose Determination by the Viscometric Affinity Assay." *Biotechnol. Prog.* (2000), 16, pp. 1119-1123.

Gabriel, Camelia and Gabriel, Sami, "Compilation of the Dielectric Properties of Body Tissues at RF and Microwave Frequencies." King's College, London, Jun. 1996, AL/OE-TR-1996-0037. http://niremf.ifac.cnr.it/docs/DIELECTRIC/Report.html.

Kobayashi, T., et al., "The influence of DC bias on the displacement and sensor output of self-sensitive piezoelectric microcantilevers." *Journal of Micromechanics and Microengineering*, 18 (2008) 035025 (7pp).

Michael, K. and Masters, A., "Applications of Human Transponder Implants in Mobile Commerce." School of Information Technology 7 Computer Science, University of Wollongong, Wollongong, NSW 2522, Australia, (2005). http://ro.uow.edu.au/infopapers/384.

Nathanson, Harvey C., et al., "The Resonant Gate Transistor." *IEEE Transactions on Electron Devices*, vol. ED-14, No. 3, Mar. 1967.

SERMACS 2007, Oct. 24-27, 2007, Greenville, SC, *General Materials Science Symposium*. Section 34, "Synthesis and Preparation of a Novel Glucose Sensing Fluid," Li, Siqi, et al.; http://www.sermacs2007.org.

van den Berg, Albert and Wessling, Matthias, "Silicon for the Perfect Membrane." *Nature*, vol. 445, Feb. 15, 2007.

Wang, Qing-Ming, et al., "Nonlinear piezoelectric behavior of ceramic bending mode actuators under strong electric fields." *Journal of Applied Physics*, vol. 86, No. 6, Sep. 15, 1999.

Yang, Eui-Hyeok, et al., "Thin-Film Piezoelectric Unimorph Actuator-Based Deformable Mirror With a Transferred Silicon Membrane." *Journal of Microelectromechanical Systems*, vol. 15, No. 5, Oct. 2006.

Zinck, C., et al., "Development and characterization of membranes actuated by a PZT thin film for MEMS applications." *Sensors and Actuators A*, 115 (2004) pp. 483-489. www.sciencedirect.com.

Rasooly, Avraham, et al., Biosensor technologies, Methods: A Companion to Methods in Enzymology, 2005, pp. 1-3, vol. 37, No. 1, Editorial 1, Academic Press, Inc., New York.

Zhou, Yongjun, et al., A MEMS viscometric sensor for continuous glucose monitoring, J. Micromech. Microeng. 17 (2007), 2528-2537, vol. 17, No. 2, Institute of Physics Publishing, Bristol, GB.

European Patent Office, International Search Report and Written Opinion for PCT/IB2009/053041, Oct. 28, 2009, 15 pages.

* cited by examiner

VISCOSIMETRIC BIOSENSOR FOR MONITORING ANALYTE LEVELS

CROSS-REFERENCE TO RELATED APPLICATION

This application is a National Stage filing of International Application Serial No. PCT/IB2009/053041, filed Jul. 14, 2009 and designating the United States, which claims priority to European Application No. 08160352.4, filed Jul. 14, 2008, the entire disclosures of which are expressly incorporated herein by reference.

FIELD OF THE INVENTION

The invention relates to a viscosimetric sensor for measuring an analyte in a fluid in vivo or in vitro or ex vivo. In particular, the invention relates to a biosensor for therapeutic, medical or diagnostic applications for monitoring analytes such as glucose, calcium or other ions, pH, and other analytes in a patient or in fluids of a patient.

BACKGROUND OF THE INVENTION

There is a need in the medical field to measure or monitor various analytes in body fluids, such as blood or urine, for diagnostic, therapeutic or medical observation purposes. Analyte measurements may take place in the patient's body (in-vivo), out of the patient's body (ex-vivo), or in a laboratory (in-vitro), depending on the application.

In the field of diabetes management, many conventional commercial blood glucose meters require taking a blood sample and are not entirely painless. Long-term implantable glucose sensors, considered as minimally invasive methods, would allow a continuous monitoring of the human glycemia and would considerably improve the quality of life of diabetics. Continuous monitoring would allow patient's to be warned of hypo- or hyperglycemia episodes even during sleep, and it would enable real-time closed-loop insulin injection system. A continuous implantable glucose sensor would be advantageous in diabetes management and overall health of the patients when compared to the present situation where many insulin dependent diabetics still rely on 2 to 6 glucose measurements per day to manage their insulin injections.

WO 2004037079 describes an implantable glucose sensor where the viscometric measurement of a sensitive fluid, as described in Beyer et al., 2000, *Biotechnol. Prog.*, 16, 1119-1123, is performed by means of respectively rotational (micro rheometer) and vibrational (micro cantilever) elements.

Another example of an application requiring analyte monitoring is hemofiltration, which is a renal replacement therapy used in the intensive care units. It is a slow continuous therapy in which sessions usually last between 12 to 72 hours. During hemofiltration, a patient's blood is passed through a set of tubing via a machine to a filter, where waste products and water are removed. Replacement fluid is added and the blood is returned to the patient. Hemofiltration concerns critically ill patients with sepsis, renal, cardiac and pulmonary failure, post-surgery or burns. During hemofiltration procedure, these patients are especially exposed to:

Hypo- and hypercalcemia (ideal Ca2+ concentration post-hemofilter ranges between 0.25 and 0.35 mmol/L, and ideal Ca2+ concentration in plasmatic patient ranges between 1.05 and 1.35 mmol/L);

Hypo- and hyperglycemia which may occur even in patients without diabetes mellitus (normal range 3.9 and 7.8 mmol/L);

Metabolic acidosis (normal pH range between 7.35 and 7.45).

Calcium plays a critical role in the initiation of clotting. Citrate is used to bind calcium and prevent blood from clotting. Citrate administered pre-filter allows the filter to be regionally anticoagulated without anticoagulating the patient.

Citrate anticoagulation is an excellent alternative to heparin anticoagulation for patients at high risk of bleeding requiring continuous renal replacement therapy. However, citrate anticoagulation has some potential adverse effects such as metabolic alkalosis and acidosis, hypernatremia, hypo- and hypercalcemia. This is why during hemofiltration, ionized calcium and pH must be well controlled in order to regulate citrate delivery. In addition, renal dysfunction may cause prolonged hypoglycemia and hyperglycemia episodes which increase the risk of infection and mortality. Today, these controls are performed by hand with expensive biosensing laboratory apparatuses, usually on an hourly basis.

SUMMARY OF THE INVENTION

An object of this invention is to provide an analyte sensor for measuring an analyte in a fluid that is reliable, compact, and economical, and that enables rapid and accurate measurement of the analyte.

Another object of this invention is to provide a viscosimetric sensor for medical or diagnostic applications for measuring an analyte in a fluid in vivo or in vitro or ex vivo.

For applications that would require continuous monitoring of analytes, it would be advantageous to provide an analyte sensor that enables frequent measurement of the analyte at short time intervals or on demand.

For in vivo applications, it would be advantageous to provide an implantable analyte sensor, such as a glucose sensor, for monitoring an analyte level in a patient, that is biocompatible, reliable, accurate, economical to produce and very compact.

Objects of this invention have been achieved by providing a viscosimetric analyte sensor according to claim 1.

Disclosed herein is a sensor suitable for the measurement of an analyte in a fluid comprising two hermetically closed chambers containing a sensitive fluid communicating with each other through at least one channel, and a semi-permeable barrier allowing the analyte to enter or to leave the chambers, each chamber having a flexible membrane allowing antagonistic variations of the volume of the chambers. One chamber is an actuation chamber and the other chamber is a measuring chamber. Within the scope of this invention, it is also possible to have both chambers act as actuation and measurement chambers, or one chamber acts as actuation chamber and both as sensing chambers, or one chamber acts as sensing chamber and both as actuation chambers. In other terms, each chamber may be provided with a single function (actuation or sensing) or a dual function (actuation and sensing).

The sensor may be implantable for in-vivo applications (for example an implantable glucose sensor), or for ex-vivo applications (for example implemented in a fluid transfer line of a medical apparatus such as a hemofiltration apparatus) or for in vitro measurements (for example implemented in laboratory biosensing equipment).

Objects of this invention have been achieved by providing a method of measuring an analyte level in a fluid according to claim 12 or 13.

Also disclosed herein is a method of measuring an analyte level in a body fluid by means of a biosensor comprising at least two chambers containing a sensitive fluid responsive to the analyte to be measured communicating with each other through at least one channel, a semi-permeable membrane allowing exchange of the analyte from between the body fluid and the sensitive fluid, each said chamber comprising a flexible membrane configured for antagonistic variations of the volume of the chambers, at least one displacement sensing element configured to measure the displacement of at least one of said flexible membranes, and at least one actuating element configured to actuate displacement of at least one of said flexible membranes, the method including displacing a first of said two flexible membranes and subsequently measuring the relaxation displacement of said first membrane or of a second of said two flexible membranes, the relaxation displacement behavior being dependant on the viscosity of the sensitive fluid. The actuation of the first flexible membrane may be in the form of a single pulsed actuation.

Also disclosed herein is a method of measuring an analyte level in a body fluid by means of a biosensor comprising at least two chambers containing a sensitive fluid responsive to the analyte to be measured communicating with each other through at least one channel, a semi-permeable membrane allowing exchange of the analyte from between the body fluid and the sensitive fluid, each said chamber comprising a flexible membrane configured for antagonistic variations of the volume of the chambers, at least one displacement sensing element configured to measure the displacement of at least one of said flexible membranes, and at least one actuating element configured to actuate displacement of at least one of said flexible membranes, the method including displacing a first of said two flexible membranes and measuring the displacement of a second of said two flexible membranes, the displacement behavior of the second membrane being dependant on the viscosity of the sensitive fluid. The first flexible membrane may be actuated by a periodical signal, such as a sinusoidal signal, whereby the phase shift of the actuation signal with respect to a sensing signal generated by the displacement of the second flexible membrane is determined, this phase shift being correlated to the viscosity of the sensitive fluid in the chambers.

The sensor may advantageously be in the form of a MEMS component. In another embodiment, the sensor body may however also be made from injected plastic or other materials.

The two chambers formed in a substrate may be closed on one side by the semi-permeable membrane so that the sensitive liquid has a large contact surface area with the semi-permeable membrane while enabling simple construction and assembly of a planar semi-permeable membrane to the substrate. The channel interconnecting the two chambers may also be advantageously located directly adjacent the semi-permeable membrane by being formed on an outer surface of the substrate.

In an embodiment, the actuating element for actuating the flexible membrane and/or the sensing element for detecting the displacement of the flexible membrane may advantageously be a piezoelectric element.

The actuating and/or sensing element may also be in the form of a MEMS device, for example comprising a suspended gate MOSFET, an electrode on the flexible membrane acting as the suspended gate.

Also disclosed herein is a biosensing device for the measurement of a plurality of analytes in a fluid, comprising a plurality of biosensors, each biosensor being configured to respond to a specific respective one of the analytes to be measured, whereby each biosensor comprises a specific sensitive fluid responsive to one of said analytes to be measured. The chambers of the plurality of biosensors may advantageously be formed within a common substrate.

In a particular embodiment of the present invention, the sensor may be configured for long term implantation in an animal or human organism, for sensing interstitial or blood analyte levels such as glucose level (or glycemia) related to the organism. The monitoring of the analyte may be intermittent, on demand or continuous.

Further objects and advantageous aspects of the invention will be apparent from the claims, following detailed description and accompanying figures.

BRIEF DESCRIPTION OF THE DRAWINGS

FIGS. 5a and 5b are simplified graphical illustrations of actuation signals and sensing signals on the actuation membrane and sensing membrane respectively, according to embodiments of the invention, whereby FIG. 5a illustrates an amplitude measuring method and FIG. 5b illustrates a phase shift measuring method;

DETAILED DESCRIPTION OF EMBODIMENTS OF THE INVENTION

Referring to the figures, especially FIGS. 1-4, an analyte sensing system 1 comprises at least one sensor 1a comprising a body portion or substrate 8, at least two hermetically closed chambers 2a, 2b and one or more channels 5 interconnecting the chambers formed in the body portion. The chambers include an activation chamber $2a$ and a measuring chamber $2b$, containing a sensitive fluid 3, the chambers communicating with each other through the at least one channel 5. The sensor further includes a semi-permeable or nanoporous barrier 4 allowing the analyte to be measured to enter or leave the chambers, but retaining the sensitive fluid in the chambers. Each chamber comprises at least one flexible membrane 6, 7 configured for antagonistic variations of the volume of the chambers. The semi-permeable or nanoporous barrier 4 is preferably rigid, however it is also possible to have a semi-permeable or nanoporous barrier that is elastic and that subject to measurable deformation during the pressure variations in the chambers. The body portion or substrate could be made of various materials, depending on the application, for example of an injected plastics material, of metal alloy, of a ceramic material, or of a semiconductor. For in-vivo applications and certain ex-vivo applications, the materials in contact with body fluids are selected from biocompatible materials, or coated with a biocompatible coating 20 that may also provide an anti-fouling function, especially to prevent growth or fouling on the semi-permeable or nanoporous barrier 4.

In some embodiments the channels 5 interconnecting the two chambers may be configured as capillary channels that apply a certain resistance to flow of sensitive fluid between the actuation and sensing chambers. This configuration is suited to a measuring method (discussed in more detail further on in relation to FIG. 4) based on measuring the relaxation displacement characteristic of the sensing membrane after actuation.

Figure 5A:
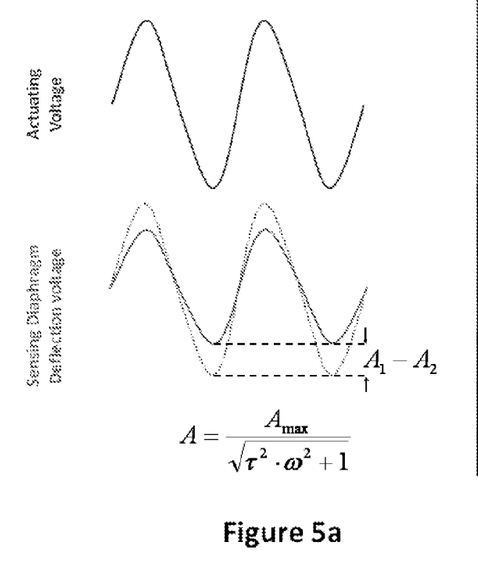
Figure 5B:
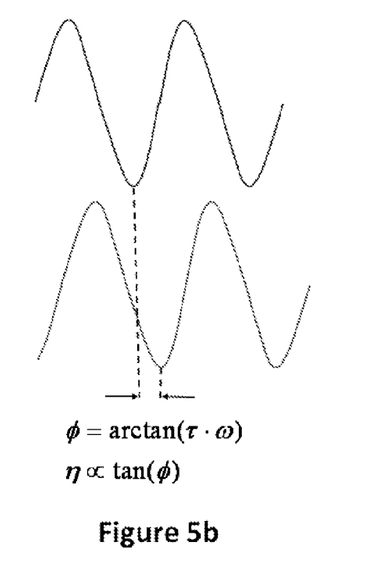

In other embodiments the channels 5 may be configured such that the flow resistance of sensitive fluid passing from one chamber to the other is small or negligible or insignificant, whereas this configuration is suited to a measurement method (discussed in more detail further on in relation to FIGS. $5a$, $5b$) based on amplitude or phase shift measurement of the actuation and sensing signals.

Figure 15:
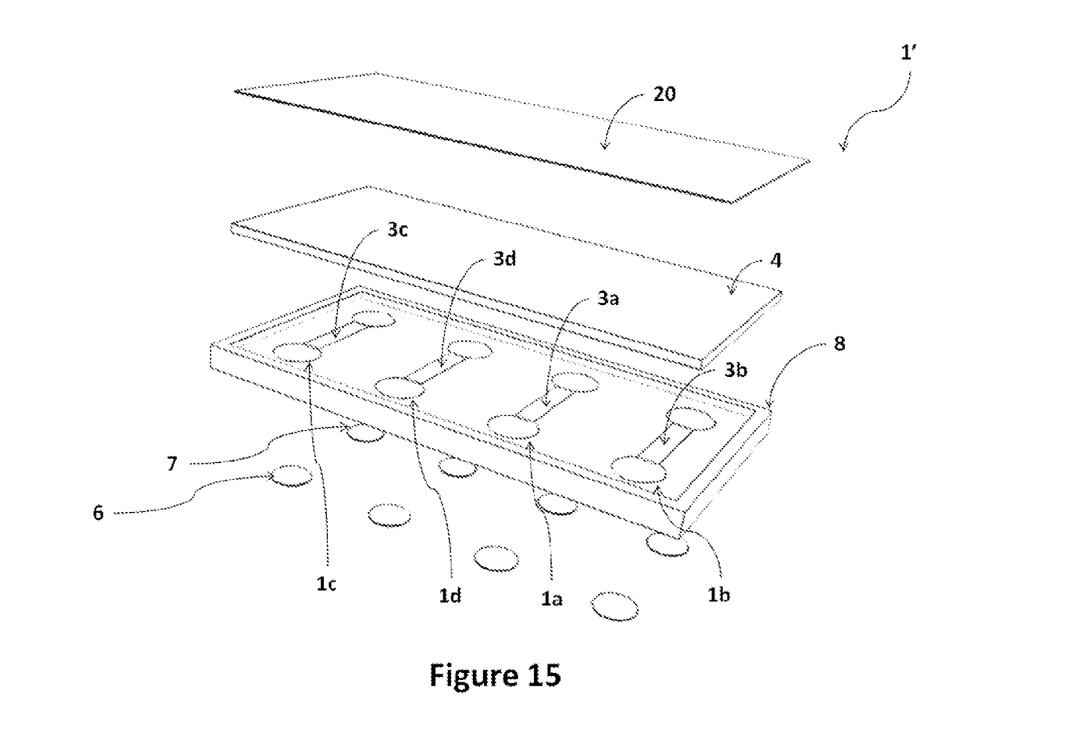
FIG. 15 is a schematic view in perspective of a biosensor with a plurality of sensors for multiple analyte measurement according to an embodiment of the invention.

As illustrated in FIG. 15, the analyte sensing system 1' may comprise a plurality of sensors $1a$, $1b$, $1c$, $1d$. Each sensor may be configured to measure a different analyte or property of the fluid to be measured, for example glucose concentration, calcium ion concentration, pH and temperature. The multi-analyte sensing system may be formed as a single unit for measurement of a plurality of analytes and other properties of the fluid simultaneously. The body portion or substrate 8 may advantageously be common to all sensors, however it would also be possible to form the sensors from separate substrates that are assembled or bonded together. Each sensor may advantageously be formed identically, but it is also possible for the sensors to have different shapes and dimensions if appropriate for the analytes or properties to be measured. The nanoporous barrier 4 may advantageously be common to all sensors, however it would also be possible to have different nanoporous barriers for the different sensors. The sensitive fluids $3a$, $3b$, $3c$, $3d$ in the different sensors are different from each other in that each is configured specifically for the specific analyte to be measured by the respective sensor.

The temperature sensor $1d$ does not rely on analyte exchange through the nanoporous membrane. In a first variant, the temperature acts on the sensitive fluid such that the viscosity is correlated to the temperature. In another embodiment, the temperature may simply effect a change in volume of the liquid in the chamber due to a change in temperature. The temperature sensor does therefore not require an actuation chamber, nor a nanoporous membrane and may be configured accordingly. Nevertheless, the configuration of the temperature sensor may be similar or identical to the other sensor chamber to simplify making and operating the sensor.

The single or multi-analyte sensing system according to the invention may be advantageously produced in a very compact and economical manner, especially suited for disposable sensing devices.

In addition, the combination of several biosensors on a same substrate, each filled with a specific sensitive fluid, may lead to a continuous multi-analyte detection device (see FIG. 15).

Examples of applications in which the sensing system according to the invention may be used are:
as an implanted sensor for continuous in-vivo monitoring for instance of blood glucose concentration, or
for ex-vivo monitoring, for instance for in-line monitoring of inorganic ions, glucose, pH and temperature in blood plasma for hemofiltration applications; or
for Lab-on-Chip applications to enable low cost biological analysis, avoiding expensive laboratory equipment and reagents; or
in the control of continuous water and liquid food quality, for example to detection organic solvents like ethanol in aqueous solutions, or
in continuous monitoring of glucose, pH and temperature in mammalian cell bioreactors (e.g. embryonic stem cells).

Sensor Structure

Chambers can be filled with a sensitive fluid through an inlet and gas evacuated through an outlet, the inlet and outlet being sealed off after the filling process is complete. The two chambers do not necessarily need to have the same dimensions which may vary from e.g. 100 µm to 1,000 µm in diameter and from 50 to 500 µm in height for a cylindrical actuating chamber, and from e.g. 100 to 1,000 µm in diameter and from 50 to 500 µm in height for a cylindrical sensing chamber. The chambers are preferably essentially cylindrical, but may have any shape.

One chamber called activation or "actuation chamber" or "actuating chamber" $2a$ is a chamber where the activation of the flexible membrane of this chamber will induce volume variations of the sensitive fluid contained in this chamber.

The other chamber called "measuring chamber" or "sensing chamber" $2b$ is a chamber where a volume variation of the sensitive fluid which is induced in the actuating chamber induces in response a volume variation of the sensitive fluid contained in this chamber due to the fluid communication between the two chambers via at least one channel. The resulting volume variation or parameter correlated thereto (e.g. membrane displacement) of the sensitive fluid contained in the sensing chamber will be measured to determine the viscosity of the sensitive fluid.

The sensitive fluid 3 is a fluid exhibiting a viscosimetric affinity for the analyte of interest. There are a number of "Stimuli-responsive" hydrogels capable of reversibly converting chemical energy into mechanical energy (e.g. polymeric or polyelectrolytic) that are sensitive to various analytes such as ionized calcium, glucose, or pH. These fluids are generally also responsive to temperature.

For example, sensitive fluids exhibiting viscosimetric affinity for glucose are polymeric phenylboronic acid derivatives and ConA-based polymeric fluids as described in Li et al., 2007, *Chemistry and Biochemistry*, University of South Carolina, Columbia, S.C., USA. Abstracts, 59th Southeast Regional Meeting of the American Chemical Society, Greenville, S.C., United States, October 24-27, GEN-034. Publisher: American Chemical Society, Washington, D.C. or in Beyer et al., 2000 (cited above). For ionized calcium, sensitive fluids include polyelectrolytic mixtures based e.g. on Chondroitin Sulphates or genetically engineered proteins within hydrogels capable of producing a stimulus-responsive action mechanism like swelling or viscosity change.

The semi-permeable barrier 4 comprises a membrane which allows the analyte to enter the chambers and prevents the sensitive fluid from exiting the chambers. In in-vivo applications, the membrane is also biocompatible. Semi-permeable membranes according to the invention may be a rigid nanoporous semi-permeable barrier, e.g. commercially available anodic alumina (such as an anopore inorganic membrane (Anodisc®) having a precise, non-deformable honeycomb pore structure with no lateral crossovers between individual pores and composed of a high-purity alumina matrix that is manufactured electrochemically or nanoporous ceramic membrane made from anodic aluminum oxide) or ultrathin silicon nanoporous membranes such as described in Van den Berg et al., 2007, *Nature* 445, 726 or stiffened cellulose (e.g. an assembly of anopore or anodic membrane and cellulose membrane). The semi-permeable barrier according to the invention must not be corroded by biological fluids. In an embodiment, it may have a support coating to promote vascularization, to ensure biocompatibility and to prevent biofouling of the surface (e.g. induced by local inflammatory response).

As the viscosity of the abovementioned sensitive fluid also depends on temperature, a silicon band gap temperature sensor such as a temperature sensor included in a silicon integrated circuit (such as Brokaw band gap reference) measuring the band gap voltages at two different currents and calculating the temperature of the diode (e.g. a PN junction diode) may be directly integrated on the substrate of one of the two chambers. The temperature may also be determined by a sensor $1d$ (see FIG. 15) similar to the analytes sensors ($1a$, $1b$, $1c$), whereby the temperature affects the viscosity of the liquid in the chamber.

In another embodiment, temperature may also affect the volume of liquid in the chamber causing expansion or contraction of the liquid and displacement of the flexible membrane. In this case, the membrane position is measured and correlated to the temperature.

These two chambers, may communicate through at least one channel 5. In an embodiment, the channel is a "microchannel" that acts as a resistance to flow of sensitive fluid between the actuation and sensing chambers $2a$, $2b$. The channel may be configured in many different shapes and profiles (e.g. cylindrical or parallelepipedic, of constant or variable cross-section) and may be straight or curved (e.g. "S" shaped) to increase the communication path between chambers. In an embodiment, the microchannel(s) may be micromachined on a substrate 8 such as by standard microfabrication technologies like Micro-Electro-Mechanical Systems (MEMS) and the like. For certain applications, the microchannel may have a section of few to few tens $\mu m^2$ (1 $\mu m = 10^{-6}$ meter) and a length from few tens to few hundreds $\mu m$.

The volume of the sensitive fluid confined in the actuating chamber $2a$ may be changed by moving (inflating or deflating) the flexible actuating membrane 6. The flexible membrane of the chamber may be made of a polymer (e.g. such as a polyimide film like flexing Kapton® (DuPont) or an elastomer substrate) or ultrathin silicon coated with a conductive, piezoelectric or magnetic material on the one side, and coated with an inert material not interfering with the sensitive fluid (e.g. a polyxylene polymers such as Parylene (Para Tech Coating, Inc)) on the other side. Its dimensions may be e.g. 500 $\mu m$ in diameter and few $\mu m$ in thickness (e.g. 10 $\mu m$) and depends on the volume of sensitive fluid to be displaced.

The flexible membrane 7 of the sensing chamber, also called "sensing membrane" may be made of a polymer (e.g. such as a polyimide film like flexing Kapton® (DuPont) or an elastomer substrate) or ultrathin silicon coated with a conductive, piezoelectric or magnetic material on the one side, and coated with an inert material not interfering with the sensitive fluid (e.g. a polyxylene polymers such as Parylene (Para Tech Coating, Inc)) on the other side. Its dimensions may be e.g. from 100 to 1,000 $\mu m$ in diameter and few $\mu m$ in thickness (e.g. 10 $\mu m$) and depends on the volume.

The flexible sensing and actuating membranes do not need to be identical. They can differ both in geometry as well as in their structures (bimorph or unimorph, or other structures).

In certain embodiments, the flexible membranes 6, 7 may also be part of an actuating Metal Oxide Semiconductor Field Effect (MOSFET) such as described in more detail below.

Sensor Operation

Figure 1:
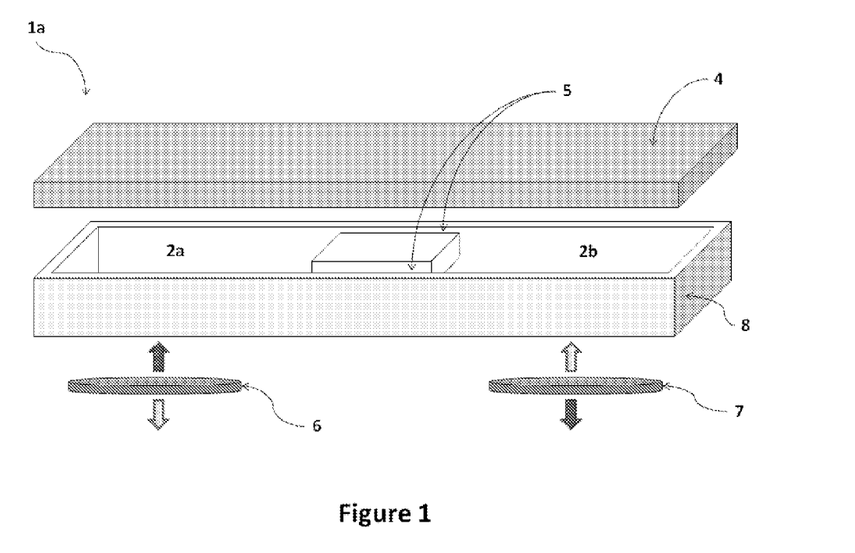
FIG. 1 is a schematic view in perspective of a biosensor according to an embodiment of the invention.
Figure 2:
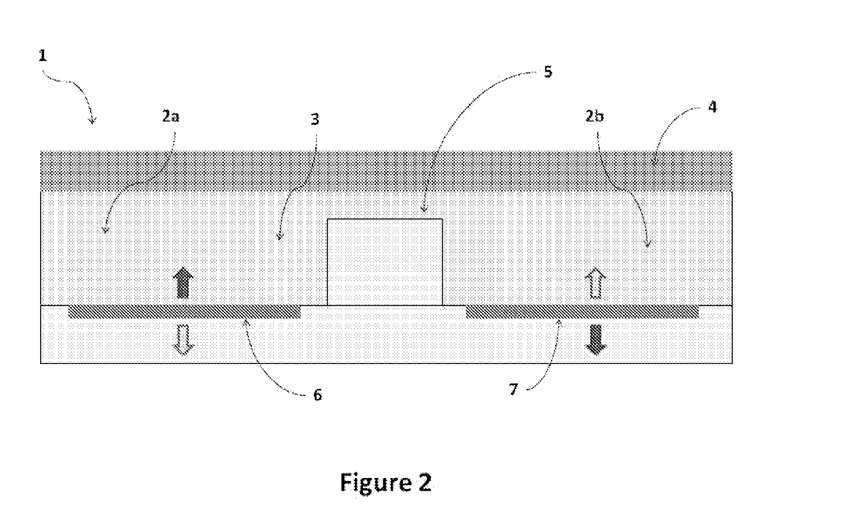
FIG. 2 is a schematic view in cross-section of the biosensor of FIG. 1.
Figure 3:
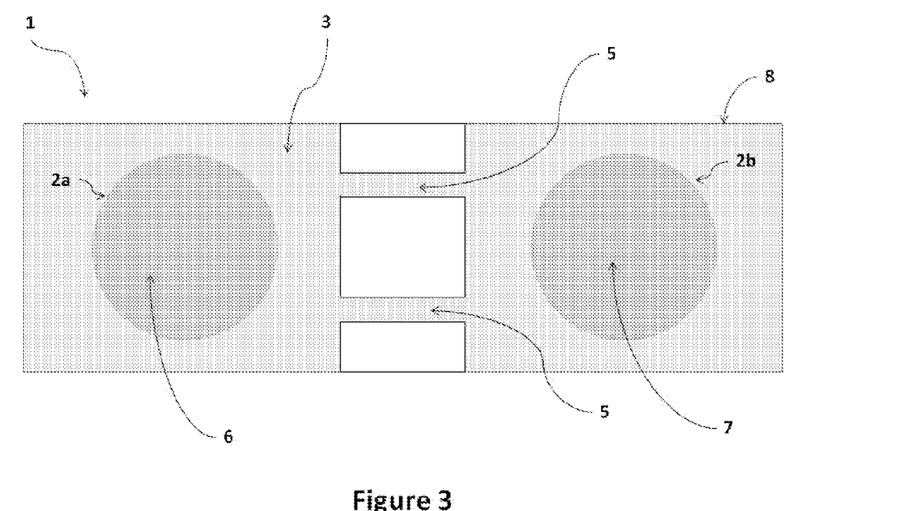
FIG. 3 is a schematic top view of the biosensor of FIG. 1 without nanoporous semi-permeable barrier.
Figure 4:
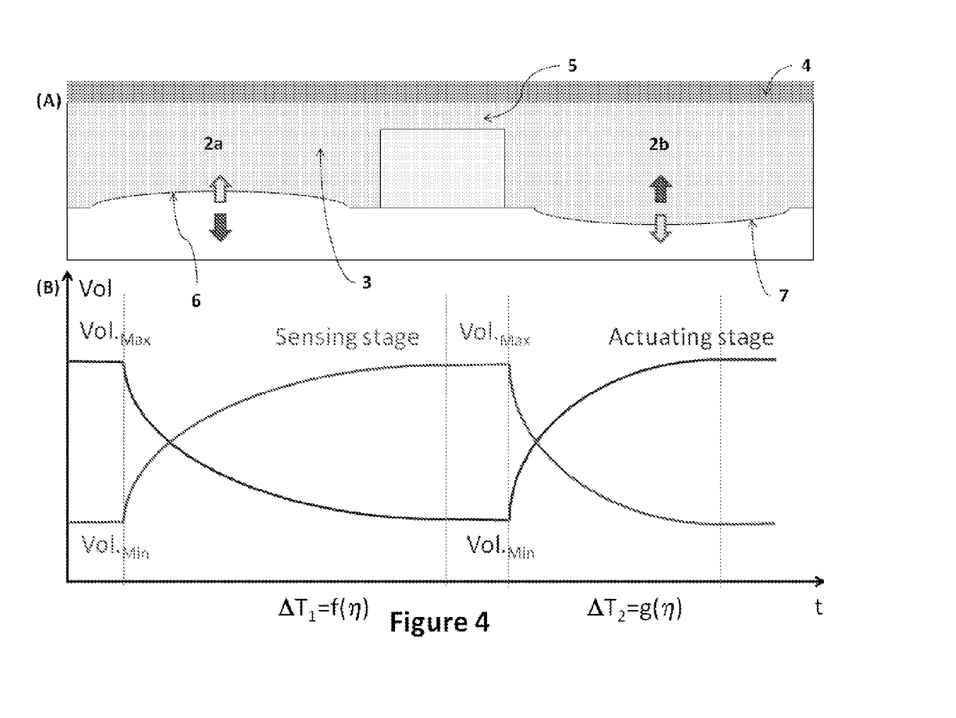
FIG. 4 is a schematic view in cross-section of the biosensor of FIG. 1 and accompanying membrane displacement graph illustrating an example of a measurement process when the actuating membrane is actuated.

The actuation of the flexible membrane 6 of the actuating chamber $2a$ results in an increase or decrease of volume inside this chamber. According to an embodiment, the sensitive fluid is not compressible and both chambers are hermetically sealed by a substantially rigid nanoporous semi-permeable barrier (semi-permeable membrane) 4, therefore the change of volume yields a transfer of volume, or a flow, from the actuating chamber $2a$ to the sensing chamber $2b$ or conversely, through at least one microchannel 5 interconnecting the two chambers. Due to its section, the microchannel(s) exhibit(s) a resistance to the flow which depends upon the viscosity of the sensitive fluid. As illustrated in FIG. 4, the sensing and the actuating membranes deform antagonistically: when the first inflates, the second deflates and conversely. Consequently, the deformation of the flexible sensing membrane 7 of the sensing chamber $2b$ during the actuation stage, will occur with a delay, the duration of which is strongly correlated to the sensitive fluid viscosity: the more viscous the sensitive fluid, the longer the time to transfer a given volume, and conversely.

When the excitation of the flexible membrane 6 of the actuating chamber $2a$ is switched off, the flexible membranes from each chamber will tend to recover their equilibrium position, due to their elastic material properties. The time required for the flexible membranes to reach this equilibrium state, namely the relaxation time, also depends on the viscosity of the sensitive fluid passing through the microchannel(s): the more viscous the sensitive fluid, the longer the membranes' relaxation time.

An example of the overall measurement process is illustrated in FIGS. 4 (A) and (B).

In this example, $\Delta T_1$ depends on the actuating force, the sensitive fluid viscosity $\eta$ and flexible membrane material intrinsic parameters.

$\Delta T_2$ depends only on the sensitive fluid viscosity $\eta$ and flexible membrane material intrinsic parameters. In order to work properly and accurately, the device may need to be calibrated.

Consequently, $\eta$ may be simply computed from $\Delta T_1$ and/or $\Delta T_2$.

As the sensitive fluid viscosity $\eta$ is correlated to the analyte concentration (such as glucose concentration) whereas the sensitive fluid exhibits a viscometric affinity for analyte of interest such as glucose ($\eta$ is for example inversely proportional to analyte concentration in the case of ConA: in presence of the analyte, $\eta$ decreases and conversely), the actuating and sensing (relaxation) times are also correlated to the analyte concentration. If the sensitive solution is based on polymeric phenylboronic acid derivatives, it is the contrary, i.e. in presence of the analyte, $\eta$ increases.

The measurement method discussed above thus relies on the relaxation time of the system to reach an equilibrium position after it has been actuated by a step-like waveform.

Another method comprises exciting the system with a harmonic (sinusoidal) waveform and measuring the amplitude (FIG. 5a) or the phase (FIG. 5b) of the sensing membrane. In this case, a sinusoidal excitation (e.g. voltage on a piezoelectric membrane) may be applied to the actuating membrane while the signal generated by the movement of the sensing membrane is sampled and recorded. The amplitude of the sensing membrane signal depends on the system geometry, as well as on the fluid viscosity and excitation frequency. In the same way, the phase shift between the actuating voltage (harmonic excitation) and the signal (e.g. voltage) produced by the bending of the sensing membrane is measured. As for the amplitude, the phase shift is found to depend on the device geometry, on the viscosity and on the excitation frequency as illustrated in FIG. 5b. In the amplitude and phase shift measurement method, it is possible for the channel or channels 5 between chambers 2a, 2b to have a relatively large section so as to generate a low or negligible flow resistance compared to the microchannels employed in the embodiments relying on measurement of the relaxation time after the actuation impulse (described above in relation with FIG. 4).

In both pulsed and phase shift methods, the response depends on viscosity. Both methods enable a very accurate viscosity measurement (error under 1%).

Exemplary embodiments of the biosensor according to the invention are described in the following sections.

Piezoelectric Actuating and Sensing

Figure 6:
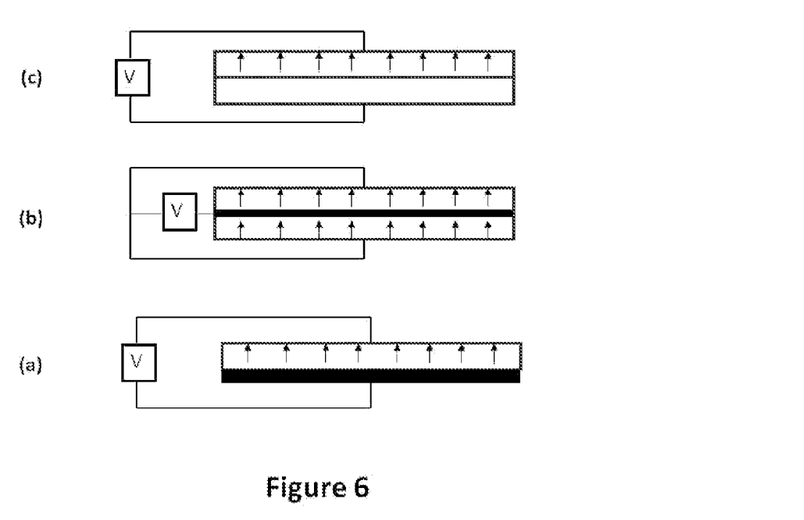
FIG. 6 illustrates schematic examples of possible piezoelectric structures for actuating and sensing membranes.

A piezoelectric effect may be used to complete both actuation and sensing for viscosity measurements as exemplified by the embodiments illustrated in FIGS. 4 and 6. The actuation of the actuating membrane 6 as well as sensing of the induced deformation of the sensing membrane 7 may be accomplished through the deformation of piezoelectric ceramic bimorph or unimorph structures such as those described by Wang et al., 1999, *Journal of Applied Physics* 86(6): 3352-3360.

Applying an adequate potential to the piezoelectric layers of the actuating membrane will generate a force which will tend to change its shape, thus generating a displacement that will change the volume in the actuating chamber.

Figure 12:
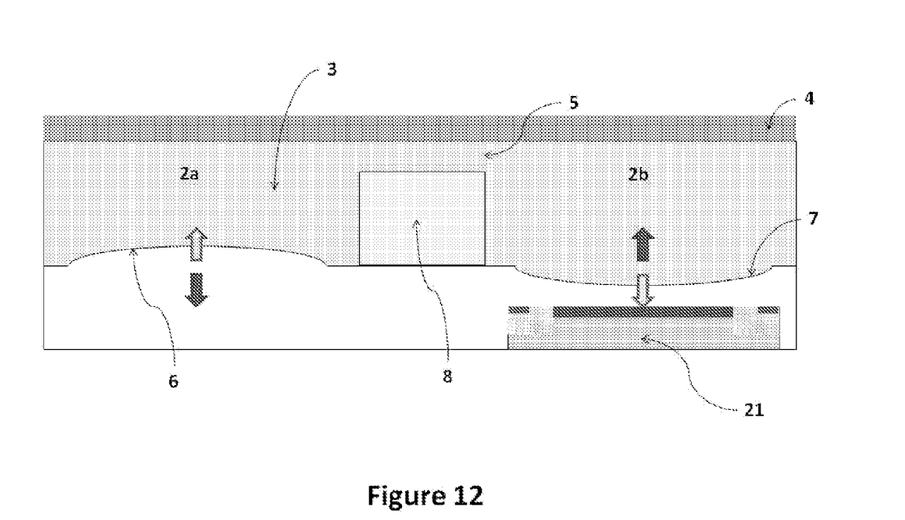
FIG. 12 is a schematic view in cross-section of a biosensor according to an embodiment of the invention where the sensing membrane displacement sensor comprises a MOSFET and the actuation membrane is actuated by piezoelectric effect.

As illustrated in FIG. 6, a bending actuation mechanism is an effective way to achieve displacement in piezoelectric actuators. Bimorph (FIGS. 6 (b) and (c)) and unimorph (FIG. 6 (a)) are examples of bending mode actuators, which are constructed by bonding together two thin piezoelectric plates or one piezoelectric plate and one elastic plate, (e.g. the actuating membrane in this case), in such a manner that when the actuators are driven, the piezoelectric transverse strain will be converted to large bending displacement in the perpendicular direction due to the constraint of each component in the actuator structure. In the bimorph variants, it is possible to have a series connection (FIG. 6 (c)) whereby the bending actuation can be effected in both directions of the membrane displacement, or a parallel connection (FIG. 6 (b)) whereby the bending actuation is effected in only one direction of the membrane displacement. A sketch of some possible arrangements for piezoelectric actuation and sensing are depicted in FIGS. 4, 6 and 12.

In embodiments where both actuation and sensing viscosity measurements are carried out by piezoelectric effect, the flow of sensitive fluid outside/inside the sensing chamber will induce an opposite deformation of the piezoelectric sensing membrane with respect to the actuating one (antagonism). Then, due to the piezoelectric effect, this mechanical energy is converted into electrical energy by inducing a potential difference across the piezoelectric layers of the sensing membrane. Measuring the electrical signal in terms of potentials, charges or currents variations may be used to compute the deformation of the sensing membrane, and so the volume transferred from one microchamber to the other as a function of time.

The piezoelectric effect can be not only used to sense a deformation, but this can also be addressed by measuring the change in the resistivity of a dedicated structure such as deformation gauges (namely the piezoresistive effect) which can be integrated onto the sensing membrane.

Since the time dependence of the induced voltage of the sensing membrane with respect to the time dependence of the applied voltage of the actuating membrane depends on the viscosity, this information may be used to extract the viscosity of the sensitive fluid.

Once the measurements are achieved, the flexible membranes will recover their steady states after a certain time.

However, an interesting aspect of piezoelectric actuation is that the displacement depends on the bias polarity. Then, reversing the polarity will also reverse the deformation which is an important aspect since it provides a simple way to restore the initial position of the actuating membrane in a controlled way.

Sensing can also be performed during this recovery phase.

In addition, membranes can also be used as actuators and sensors during the same actuating/reading phases. For example, one membrane is inflated while the other is deflated by applying adequate potentials on each of the membranes (this can be done by applying a positive potential on one membrane and a negative potential on the other membrane if the membranes are similar). This will induce a transfer of the sensitive fluid from one chamber to the other. Later, the potentials are removed and both membranes will tend to recover their steady sates. During this relaxation phase, both membranes can be used to sense the fluid viscosity through the time dependence of the induced relaxation signals generated from both membranes at the same time.

Measurement Under Periodic Excitation

The viscosity can also be measured through the frequency response of the sensing membrane when the actuating membrane is excited periodically, as discussed above in relation to FIGS. 5a, 5b. Amplitude and phase of the sensing signal will also depend on the sensitive fluid viscosity, providing other criteria to characterize the sensitive fluid viscosity.

When the excitation signal has a sine waveform, nonlinearities of the system will generate harmonics that can bring new insights into the overall system response.

Piezoelectric Actuating and MOSFET Sensing

In another embodiment, as an alternative to one or both piezoelectric membranes, the sensing may be performed by a so-called suspended gate Metal Oxide Semiconductor Field Effect Transistor (MOSFET).

MOSFET Operation

The "standard" MOSFET

Figure 8:
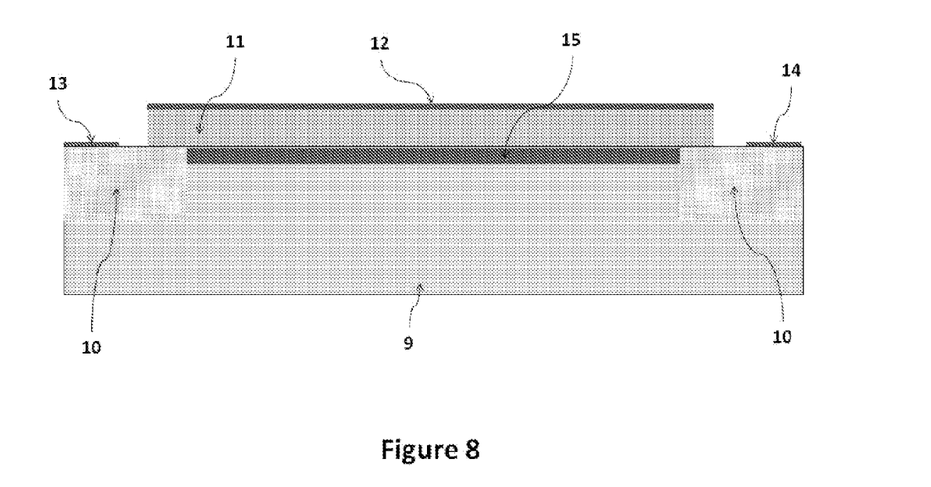
FIG. 8 is a schematic view in cross-section of a standard MOSFET.

The MOSFET represents the central element of microelectronics integrated circuits. FIG. 8 depicts the cross section of a standard MOSFET.

It consists of a semiconductor substrate (here we assumed P-type doped) where two N-type implants 10 define Drain 13 and Source 14 contacts. In addition, an insulating layer 11 (for example $SiO_2$) of about 20 nm thick is formed on top of the substrate 9, on which a conductive layer is deposited to form the gate contact 12.

As such, no current will flow between source and drain since any electric path between them will face some reversed bias P-N junction.

The role of the gate electrode is to create an N-type conducting path 15 between the N-type doped source and drain implants, namely the channel, in order to allow some current to flow. Then, for a given drain to source voltage, the gate voltage $V_G$ monitors the drain (or source) current $I_D$. The higher the gate potential, the more the current flows. A typical $I_D(V_G)$ characteristic is depicted on FIG. 9.

Figure 9:
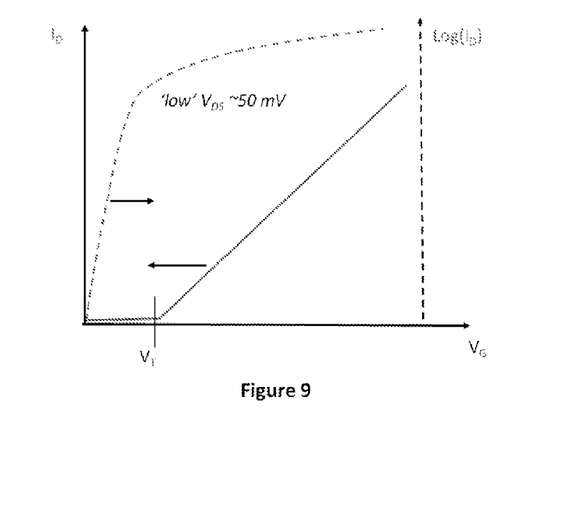
FIG. 9 is a current-voltage graph describing the drain current ($I_D$) characteristics of the MOSFET of FIG. 8 as a function of the gate voltage ($V_G$)

At low $V_{DS}$, typically 50 mV, the basic relation that links the drain current to the gate voltage when higher than the threshold voltage can be simply expressed as:

$$I_D \propto (V_D - V_S) \cdot (V_G - V_T(T_{SiO2})) \cdot \frac{\varepsilon_{SiO2}}{T_{SiO2}} \text{ for } V_G > V_T$$

Where $V_T(T_{SiO2})$ is a characteristic of the transistor called the threshold voltage. We intentionally included a formal dependence on oxide thickness even though this is never mentioned explicitly.

Below $V_T$, the current varies exponentially with the gate voltage:

$$I_D \propto \exp\left(\frac{V_G - V_T(T_{SiO2})}{n \cdot U_T}\right) \cdot \frac{\varepsilon_{SiO2}}{T_{SiO2}} \text{ for } V_G < V_T$$

Where the factor n has a value close to unity and $U_T$ is the thermodynamic voltage which value is close to 26 mV at 20° C.

The Suspended Gate MOSFET

Figure 10:
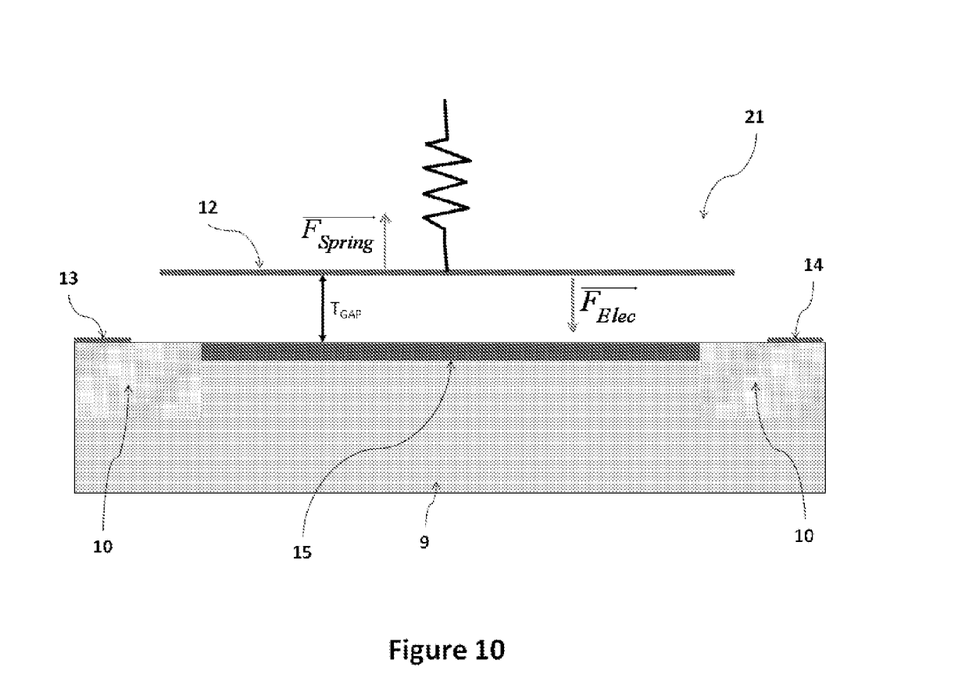
FIG. 10 is a schematic view in cross-section of a suspended gate MOSFET.

Referring to FIG. 10, a suspended gate MOSFET 21 is illustrated. According to the aforementioned relations, not only the gate voltage can change the current, but also the separation between the gate electrode and the conducting channel 15 (Nathanson et al., 1967, *The resonant gate transistor. Electron Devices, IEEE Transactions on*. Publication Date March 1967 Volume: 14, Issue: 3 on page(s): 117-133). This separation can be varied depending on the forces acting on the gate 12, such as the electrostatic force (FIG. 10) or the pressure exerted from a fluid. Furthermore, if the gap between the gate electrode 12 and the channel 15 could be varied, we would obtain another interesting characteristic: for a given $V_G$, the drain current becomes a function of the gate to conducting channel gap distance $T_{GAP}$.

Figure 11:
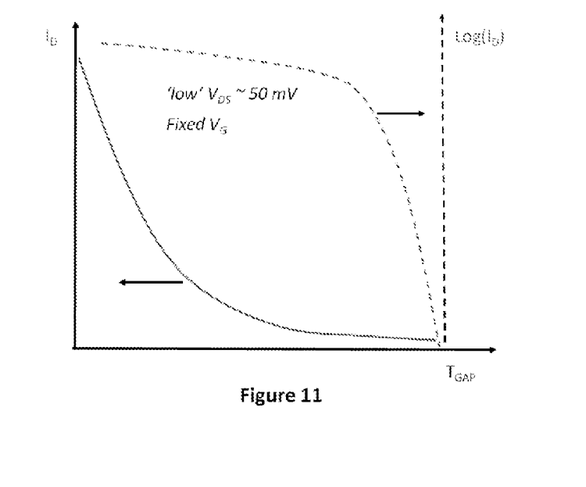
FIG. 11 is a current gap graph describing the drain current ($I_D$) characteristic of the MOSFET of FIG. 10 as a function of the gap ($T_{gap}$) between the gate and the substrate.

FIG. 11 illustrates characteristics of the source current as a function of the gap distance $I_D(T_{GAP})$.

For a given gap separation (and fixed bias), the current has a unique value. This correspondence between DC current and $T_{GAP}$ is useful to perform accurate measurements of a membrane deformation.

Based on the properties of the suspended gate MOSFET, according to an embodiment, the actuation of the flexible membrane 6 of the actuating chamber may be achieved from a piezoelectric membrane, but the induced deformation of the sensing membrane 7 may be sensed through the drain current variation of a related suspended gate MOSFET device 21 such as depicted on FIG. 10 (acting in this case as a pressure sensor). An example of such an arrangement is shown in FIG. 12.

MOSFET Actuating and Sensing

Figure 13:
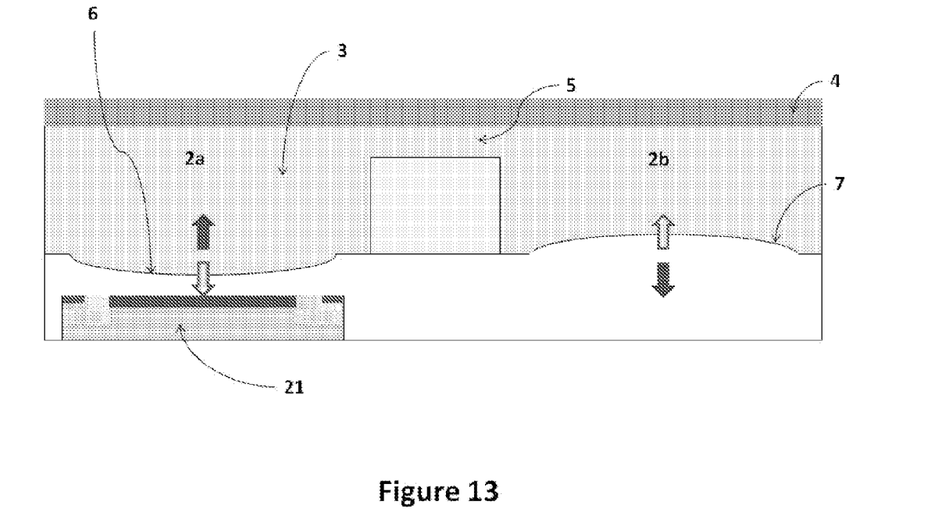
FIG. 13 is a schematic view in cross-section of a biosensor according to an embodiment of the invention where the actuation membrane displacement sensor comprises a MOSFET and the sensing membrane is passive.

FIG. 13 is a schematic view in cross-section of a biosensor according to an embodiment of the invention where the displacement sensor of the actuation membrane 6 comprises a suspended gate MOSFET 21 and the sensing membrane 7 is passive.

In another embodiment, the suspended gate MOSFET may also play the role of the actuating 6 and sensing membrane 7 since there is an electric force between the suspended gate 12 and the substrate 9 that is induced by the charges in the conducting channel 15 and on the gate 12. When applying a gate voltage on the actuating suspended gate MOSFET 21, the electrode on the flexible actuation membrane 6 will then tend to move towards the conducting channel 15 and the MOSFET 21 acts as an actuator. The volume of the actuating chamber 2a will then increase, inducing the sensitive fluid to flow from the sensing chamber 2b into the actuating chamber 2a. During this step the MOSFET acts as an actuator. After this actuation step, the MOSFET acts as a sensor, whereby the current changes with time through the time dependence of $T_{GAP}$, which in turn depends on the sensitive fluid viscosity.

MOSFET Actuating and MOSFET Sensing

Figure 14:
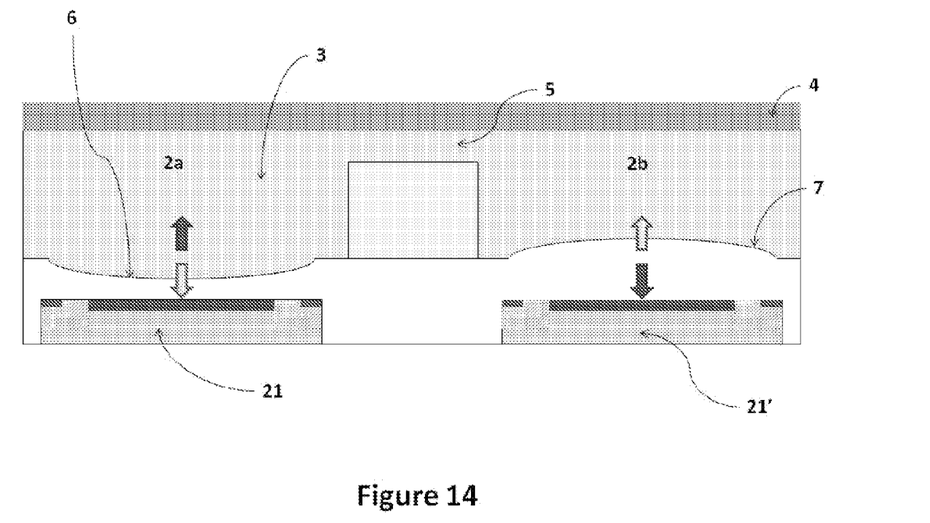
FIG. 14 is a schematic view in cross-section of a biosensor according to an embodiment of the invention where the actuation membrane displacement sensor comprises a MOSFET and the sensing membrane also comprises a MOSFET.

FIG. 14 is a schematic view in cross-section of a biosensor according to an embodiment of the invention where the displacement sensor of the actuation membrane 6 comprises a suspended gate MOSFET 21 and the displacement sensor of the sensing membrane 7 also comprises a suspended gate MOSFET 21'. One of the suspended gate MOSFET's 21 acts as the actuating device 21 whereas the other plays the role of the sensing device 21' In contrast to the precedent embodiment, variation of the volume in the sensing chamber 2b will actuate a suspended gate MOSFET of the sensing device 21' used to sense the sensing membrane 7 deformation through the variation of the drain current, thus giving an indication of the viscosity of the sensitive fluid.

Resonant MOSFET

Similar to the piezoelectric solution, applying periodic excitation to the suspended gate MOSFET can be used to characterize the viscosity of a viscous fluid.

The frequency response of the suspended gate immersed in the fluid when applying a potential that varies periodically over time with a pulsation is used to measure the viscosity of the fluid through the measurement of the quality factor and the resonant frequency of the suspended gate. Also the measurement of the phase can be used to sense the viscosity, as for the piezoelectric actuation. This can be achieved by means of the drain current or of the gate capacitance measurements.

Implementation and Methods of Use

In a further aspect of the invention, the two chambers of the sensor according to the invention are hermetically sealed by a rigid nanoporous semi-permeable barrier. The semi-permeable barrier confines inside the chambers the sensitive fluid which viscosity depends on analyte concentration, and allows the analyte contained in the interstitial fluid or in blood permeating through.

In a further aspect of the invention, the two chambers of the sensor according to the invention are hermetically sealed by a planar rigid nanoporous semi-permeable barrier.

In another further aspect of the invention, the at least microchannel is located just next to the nanoporous semi-permeable barrier at the surface of which operates the viscometric affinity process.

In another further aspect of the invention, the at least microchannel is a plurality of microchannels.

In another further aspect of the invention, the at least microchannel is one or several capillaries.

In another further aspect of the invention, the sensor further comprises an actuating element suitable for actuating the flexible membrane 6 of the first chamber 2a (e.g. actuation chamber) to induce variation of the volume of the sensitive fluid in the actuation chamber.

In another further aspect of the invention, the sensor further comprises a sensing element suitable for sensing the movement of the flexible membrane 7 of the second chamber 2b (e.g. sensing chamber) induced by the variation of the volume of the sensitive fluid in the actuation chamber.

In the context of the invention, measurement of the analyte concentration is based on an exchange of volume between the two chambers 2a, 2b operated by the actuation of a first flexible membrane 6, also called the actuating membrane, of the actuating chamber 2a, which works antagonistically with a second flexible membrane 7, also called the sensing membrane, of the sensing chamber 2b. The displacement characteristic of the sensing membrane is strongly correlated to the sensitive fluid 3 viscosity.

Actuation of the flexible membrane of the actuation chamber may be effected by sporadic excitation of the actuating membrane, or by periodical excitation of the actuating membrane.

In an embodiment, the actuating element for actuating the flexible membrane 6 of the actuation chamber 2a is a MEMS device.

In another embodiment, the actuating element for actuating the flexible membrane 6 of the actuation chamber 2a is a piezoelectric element.

In an embodiment of the invention, the sensing element for sensing the movement of the flexible membrane 7 of the second chamber 2b (e.g. sensing chamber) induced by the variation of the volume of the sensitive fluid in the actuation chamber 2a is a piezoelectric element.

In an embodiment of the invention, the sensing element for sensing the movement of the flexible membrane 7 of the second chamber 2b (e.g. sensing chamber) induced by the variation of the volume of the sensitive fluid in the actuation chamber is a MEMS device according to the invention.

In an embodiment of the invention, the temperature compensation may be performed through the band gap temperature sensor integrated on one of the chambers substrate. The interface with body fluids is ensured by a planar, preferably rigid, nanoporous semi-permeable barrier which may also be a part of the MEMS fabrication process.

A biosensing device for the measurement of an analyte in a fluid according to an embodiment of the invention may comprise an implantable biosensor as described herein and further comprising an electronic circuit connected to the biosensor for:

a) Intermittent monitoring of analyte levels (e.g. glycemia levels in replacement of finger pricking): the implantable sensor is controlled by an external reader which energizes the implant and performs data transmission (e.g. analyte levels) using RFID, magnetic or ultrasonic techniques; or b) Continuous monitoring: the implantable biosensor is intended to automatically record an analyte level measurement (e.g. glucose) every few minutes through an external reader, via a MICS standard compliant RF (subcutaneous implantation for interstitial analyte monitoring such as interstitial glucose) or an ultrasonic communication channel (deep implantation in bloodstream for blood analyte monitoring such as blood glucose) implemented both at the implanted sensor and external reader levels.

The continuous monitoring arrangement may be configured such that the communication channel is nearby the patient or worn by the patient.

In an embodiment for glucose monitoring, the continuous monitoring arrangement is designed to alert the patient to both hyperglycemia and hypoglycemia.

An embodiment of the invention includes a long term miniature ultra-low power implantable biosensor combining MEMS technology, flexible membranes embodied by one or two flexible gate MOSFET or by piezoelectric elements, and a sensitive fluid exhibiting a viscometric affinity for an analyte such as glucose confined in two chambers hermetically sealed by a planar rigid nanoporous semi-permeable barrier and interconnected by one or several microchannels, to measure continuously or intermittently in a minimally invasive way analyte levels such as glycemia levels in interstitial fluid or in bloodstream of patients such as diabetic patients.

Intermittent Monitoring

The biosensing device according to the invention may include a transponder for energizing the sensor with an external remote reader, and for transmitting data corresponding to the analyte levels to the external remote reader. Due to its small size (extreme miniaturization achievable with MEMS technology) and the limited or even the absence of a need for an on-board electrical power source (ultra low power consumption), the so formed biosensing transponder is particularly suitable for human implantation once encapsulated in a hermetic casing, and may remain implanted for an indefinite period of time.

The biosensing transponder may include an energy coupler for remotely and wirelessly energizing the device with a remote energy source, and a control circuit for controlling and accessing the sensor. External RF, magnetic or ultrasonic sources may be used depending on the implantation depth (e.g. subcutaneously for interstitial glucose monitoring or deeply for blood glucose monitoring).

Passive Radio-frequency identification (RFID) transponders, i.e. transponders containing no on-board power sources, while available for many years, have only recently been applied to humans (Michael et al., 2004, *Applications of human transponder implants in mobile commerce. 8th World Multiconference on Systemics, Cybernetics and Informatics*, Jul. 18-21, 2004 8*TH WORLD MULTI-CONFERENCE ON SYSTEMICS, CYBERNETICS AND INFORMATICS*, VOL V, *PROCEEDINGS-COMPUTER SCIENCE AND ENGINEERING*: 505-512, 2004). These transponders suitable for use in the context of the invention are encoded and implanted in a patient, and subsequently accessed with a hand held electromagnetic reader in a quick and non-invasive manner. Due to the small size of the transponder, the patient does not feel any discomfort or even its presence. The companion hand held reader placed above the implantation site emits a low frequency electromagnetic field that activates the passive transponder, and thereby causes it to transmit its encoded data to the reader. Hence, no battery or other permanent source of electrical power is required in the passive transponder, further reducing its size and making it even more suitable for implantation.

However, while an external RF transmitter could be used to communicate with the biosensing transponder, RF energy may only penetrate a few millimeters into a body (Gabriel et al., 1999, *Phys. Med. Biol.*, 41, 2231-2293), because of its dielectric nature. Therefore it may not be able to communicate effectively with a biosensing transponder that is located deep within the body.

In a further variant, magnetic energy could be used to control a biosensing transponder, since a body generally does not attenuate magnetic fields. The magnetic transmission may in particular be used for intermittent monitoring.

Acoustic waves (ultrasonic) may be a further variant for communicating with, and energizing efficiently a biosensing transponder that is placed deep within a human body, for instance in bloodstream, to monitor intermittently or continuously blood analyte levels in a patient such as glucose levels of diabetic patients. The biosensing transponder may be remotely acoustically energized, configured and interrogated by the external control unit secured on the patient's skin.

Continuous Monitoring

The sensor according to the invention and its control electronics may also be powered by a battery, or a remotely and wirelessly rechargeable energy storage, that will be integrated into the system, including e.g. a Medical Implant Communications Service (MICS) standard compliant RF or an ultrasonic communication subsystem, depending on the application, for remotely and wirelessly controlling, configuring and accessing the biosensor, the whole components being encapsulated in a hermetic casing to isolate the various components from intrabody environment.

This implementation may enable continuous monitoring of analyte levels (e.g. glucose) in interstitial fluid or in bloodstream as the sensor is power supplied in a permanent way.

An implantable sensor may be configured to automatically record an analyte measurement at regular interval, for instance every few minutes. The periodicity between consecutive measurements may be managed by the patient. For example, the sensor may be configured to alert the patient to both hyperglycemia and hypoglycemia as long as this latter is nearby or wears an external reader, via a MICS standard compliant RF (subcutaneous implantation for interstitial glucose monitoring) or an ultrasonic communication channel (deep implantation in bloodstream for blood glucose monitoring) implemented both at the implanted sensor and external reader levels.

The external reader may be a hand held device able to communicate wirelessly up to few meters from the patient in the case of RF communication. In the case of ultrasonic communication, the external control unit must be secured on the patient's skin.

Embodiments of invention have, inter alia, the following features and advantages:

Miniaturization and reproducibility: in an embodiment where microchannel(s) are micromachined by a MEMS fabrication process, it results in ultra low profile (around few mm$^3$) for the biosensor and its control electronics, and also in a high reproducibility (systematic wafer scale process, batch fabrication). The biosensor is advantageously self-contained (it intrinsically integrates both actuating and sensing elements) and its manufacturing costs in large series is low. Moreover, the biosensor's particularly compact arrangement is advantageous for subcutaneous implantation, especially in ambulatory conditions (e.g. for monitoring glucose levels in interstitial fluid). As the MEMS fabrication process results in a very small biosensor, such a device may be implanted directly in bloodstream, e.g. in aorta or in heart ventricles, hence eliminating the time lag between interstitial glucose and blood glucose (generally around 10-15 minutes).

Ultra low power (few µW): for embodiments with MOSFET and/or piezoelectric structures used for actuating and/or sensing, there is an advantage of very low power consumption.

Fast response time (second to fraction of ms): the sensor of the invention requires only a nanometric-scale volume of sensitive fluid to function (e.g. few nl to few hundreds nl depending on chambers and microchannel(s) dimensions), whereby a low sensitive fluid volume advantageously increases the response time of the sensor to changes in the analyte concentration surrounding the sensor.

Biotoxicity reduction: in embodiments where the sensitive fluid is Concanavalin A or Con A or other biotoxic substances, the low volume of sensitive fluid required by the sensor according to the invention is advantageous since by reducing the volume of sensitive fluid by a factor 1'000 over conventional systems, the biotoxicity risk may be limited or eliminated.

Homogeneous glucose concentration in the sensitive fluid in the two chambers and adequate mixing: in view of the small dimensions and the communication of both chambers through the nanoporous semipermeable membrane with external fluids to be analyzed, the chambers both exhibit the same analyte concentration.

Real temperature measurement of the sensitive fluid: certain embodiments of the sensor according to the invention have efficient temperature compensation, since the temperature sensor may be integrated into the biosensing system, within the analyte sensor (e.g. the band gap temperature sensor being immersed in the sensitive fluid), or on the same substrate or housing next to the analyte sensor. The temperature is measured in the surrounding tissues where the biosensor is implanted hence biasing temperature compensation process.

Planar nanoporous semipermeable barrier: the geometry and size of the sensor according to the invention allows the use of geometrically simple yet effective nanoporous semipermeable membranes.

The invention could also be advantageously used for the measurement of various analytes such as Sodium, Potassium, Chloride, Hydrogen Carbonate, and Phosphate.

Example of Architecture and Fabrication Process

Figure 7:
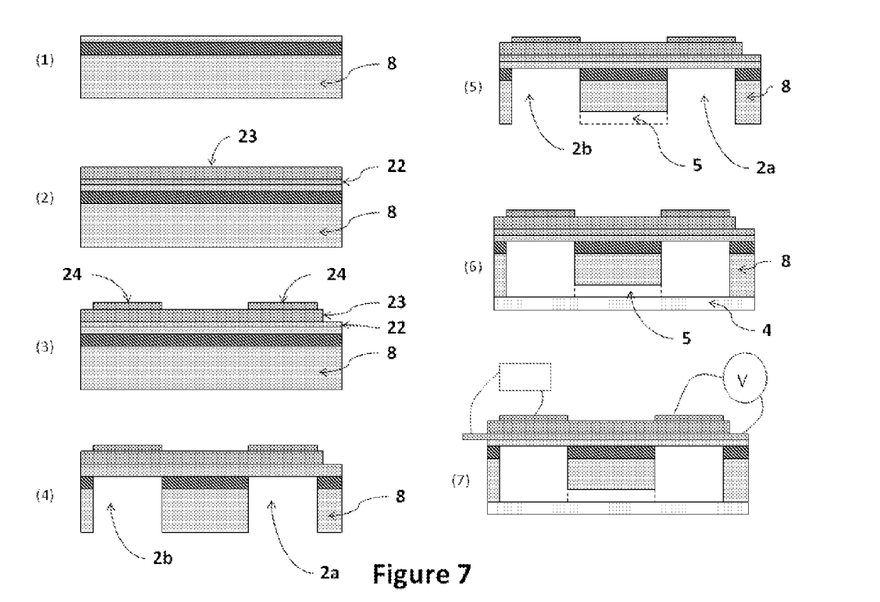
FIG. 7 illustrates an example of process flow to fabricate the piezoelectric membrane and microchambers using a SOI wafer.

Thin film piezoelectric unimorph membranes were already used for deformable mirrors (Yang et al., 2006, *Journal of Microelectromechanical Systems*, 15(5):1214-1225). FIG. 7 depicts a typical process inspired from the one described in Zinck et al., 2004, *Sensors and Actuators A* (115): 483-489, where the authors used a silicon-on-insulator (SOI) wafer on which a PZT piezoelectric layer was deposited and patterned in order to obtain a membrane that could be bent upon biasing. This type of arrangement could be advantageously used in the context of a particular embodiment of the invention: adopting a standard CMOS fabrication process, the released membranes could achieve displacements of some micrometers, which are sufficient to measure the viscosity as proposed in the present invention. The chambers may be realized through a back etching of the substrate in this case. An example of steps of a manufacturing process is illustrated in FIG. 7.

Step 1 starts with a silicon substrate 8 comprising a silicon dioxide layer ($SiO_2$) on which is deposited a conducting layer 22 and a piezoelectric layer 23 (step (2)), the conducting layer forming an electrode on a bottom side of the piezoelectric layer. A further conducting layer 24 is deposited on a top side of the piezoelectric layer and patterned by evaporation and etching, whereby portions of the piezoelectric layer may also be etched to allow access between the top and bottom electrodes on the actuation chamber for connection of the actuation circuit (step 3). The silicon layer is then etched from the bottom side to form the chambers 2a, 2b and to leave a thin layer forming the flexible membrane 6, 7 adjacent the bottom electrode (step 4). The channel(s) 5 or microchannel(s) is (are) then formed by etching on the surface of the silicon substrate between the chambers 6, 7 (step 5) and in step 6 the nanoporous semipermeable barrier layer 4 is bonded to the substrate 8 to close off the open end of the chambers. Inlet and outlet orifices (not shown) through the barrier layer or through the substrate may be provided to allow filling of the chambers with sensitive liquid and evacuation of gas, the orifices being sealed off after the filling operation.

It may be noted that in other embodiments, the substrate including the chambers and channels may be formed from an injected plastic, the actuation and displacement sensors, flexible membranes and semi-permeable membranes being deposited or assembled (welded, bonded) to the plastic substrate.

Other topologies may also be implemented, such as the use of micro-cantilevers to achieve displacements of several micrometers (Kobayashi et al., 2008, *Journal of Micromech. Microeng.* 18:035025). This solution may also be adapted in the present invention since the cantilever may also be used to impinge a force on top of a membrane and induce a deformation. Sensing may also be performed adopting a micro-cantilever structure where signals of the order of millivolts were reported.

The invention claimed is:

1. A viscosimetric biosensor suitable for the measurement of an analyte in a fluid surrounding or on the sensor, including
    at least two hermetically closed chambers, including an actuation chamber and a sensing chamber, containing a sensitive fluid responsive to the analyte to be measured, the chambers communicating with each other through at least one channel,
    semi-permeable membrane allowing the analyte to enter or leave the chambers,
    each said chamber comprising a flexible membrane configured for antagonistic variations of the volume of the chambers,
    at least one displacement sensing element configured to measure the displacement of at least one of said flexible membranes, and
    at least one actuating element configured to actuate displacement of at least one of said flexible membranes.

2. A viscosimetric biosensor according to claim 1 wherein the two chambers are hermetically sealed by the semi-permeable membrane on a side of the chambers opposite the flexible membranes.

3. A viscosimetric biosensor according to claim 1 wherein the at least one channel is located directly adjacent the semi-permeable membrane.

4. A viscosimetric biosensor according to claim 1, wherein the actuating element for actuating the flexible membrane of the actuation chamber is a piezoelectric element.

5. A viscosimetric biosensor according to claim 1, wherein the sensing element for sensing the movement of the flexible membrane of the sensing chamber is a piezoelectric element.

6. A viscosimetric biosensor according to claim 1, wherein the actuating element for actuating the flexible membrane of the actuation chamber is a MEMS device.

7. A viscosimetric biosensor according to claim 1, wherein the sensing element for sensing the movement of the flexible membrane of the sensing chamber induced by the variation of the volume of the sensitive fluid in the actuation chamber is a MEMS device.

8. A viscosimetric biosensor according to claim 6, wherein the MEMS device comprises a suspended gate MOSFET having an electrode on the flexible membrane acting as the suspended gate.

9. A unitary biosensing device for the measurement of a plurality of analytes in a fluid surrounding or on the sensor, comprising a plurality of viscosimetric biosensors portions, each biosensor portion being configured to respond to a specific respective one of the plurality of analytes to be measured, each biosensor portion comprising:
    at least two hermetically closed chambers each defining a variable volume, including an activation chamber and a measuring chamber, containing a sensitive fluid responsive to the specific analyte to be measured, the chambers communicating with each other through at least one channel;
    a semi-permeable membrane allowing the analyte to enter or leave the chambers;
    each said chamber comprising a flexible membrane configured for antagonistic variations of the volume of the chambers;
    at least one displacement sensing element configured to measure the displacement of at least one of said flexible membranes; and
    at least one actuating element configured to actuate displacement of at least one of said flexible membranes.

10. The biosensing device of claim 9 wherein each viscosimetric biosensor portion comprises a sensitive fluid responsive to one of said analytes to be measured.

11. The biosensing device of claim 9 wherein the chambers of the plurality of biosensors are formed within a common substrate.

12. A method of measuring an analyte level in a body fluid by means of a biosensor comprising at least two chambers containing a sensitive fluid responsive to the analyte to be measured and communicating with each other through at least one channel, a semi-permeable membrane allowing exchange of the analyte from between the body fluid and the sensitive fluid, each said chamber comprising a flexible membrane configured for antagonistic variations of the volume of the chambers, at least one displacement sensing element configured to measure the displacement of at least one of said flexible membranes, and at least one actuating element configured to actuate displacement of at least one of said flexible membranes, the method including displacing a first of said two flexible membranes and subsequently measuring the relaxation displacement of said first membrane or of a second of said two flexible membranes, the relaxation displacement behavior being dependant on the viscosity of the sensitive fluid.

13. A method of measuring an analyte level in a body fluid by means of a biosensor comprising at least two chambers containing a sensitive fluid responsive to the analyte to be measured and communicating with each other through at least one channel, a semi-permeable membrane allowing exchange of the analyte from between the body fluid and the sensitive fluid, each said chamber comprising a flexible membrane configured for antagonistic variations of the volume of the chambers, at least one displacement sensing element configured to measure the displacement of at least one of said flexible membranes, and at least one actuating element configured to actuate displacement of at least one of said flexible membranes, the method including displacing a first of said two flexible membranes and measuring the displacement of a second of said two flexible membranes, the displacement behavior of the second membrane being dependant on the viscosity of the sensitive fluid.

14. The method according to claim 13 wherein the first flexible membrane is actuated by a periodical signal and a phase shift of the actuation signal with respect to a sensing signal generated by the displacement of the second flexible membrane is determined.

* * * * *

UNITED STATES PATENT AND TRADEMARK OFFICE
CERTIFICATE OF CORRECTION

PATENT NO.        : 8,500,637 B2
APPLICATION NO.   : 13/054021
DATED             : August 6, 2013
INVENTOR(S)       : Eric Meurville and Jean-Michel Sallese Page 1 of 1

It is certified that error appears in the above-identified patent and that said Letters Patent is hereby corrected as shown below:

In the Claims:

In Claim 1, column 17, line 24, add the word --a-- before the word "semi-permeable".

Signed and Sealed this
Nineteenth Day of November, 2013

Teresa Stanek Rea
*Deputy Director of the United States Patent and Trademark Office*